US010363684B2

(12) United States Patent
Roberts et al.

(10) Patent No.: US 10,363,684 B2
(45) Date of Patent: Jul. 30, 2019

(54) MONITORING DISCHARGE PRESSURE ON CONCRETE MIX LOAD

(71) Applicant: VERIFI LLC, Cambridge, MA (US)

(72) Inventors: Mark F. Roberts, North Andover, MA (US); Richard K. Jordan, Littleton, MA (US); Roy J. Cooley, West Chester, OH (US); Eric P. Koehler, Miami Beach, FL (US); Meriem Bahira, Newton Upper Falls, MA (US)

(73) Assignee: VERIFI LLC, Cambridge, MA (US)

( * ) Notice: Subject to any disclaimer, the term of this patent is extended or adjusted under 35 U.S.C. 154(b) by 262 days.

(21) Appl. No.: 15/374,530

(22) Filed: Dec. 9, 2016

(65) Prior Publication Data

US 2017/0087743 A1 Mar. 30, 2017

Related U.S. Application Data

(62) Division of application No. 14/052,310, filed on Oct. 11, 2013, now Pat. No. 9,550,312.

(51) Int. Cl.
*B28C 5/42* (2006.01)
*F24S 25/61* (2018.01)
(Continued)

(52) U.S. Cl.
CPC ............ *B28C 5/422* (2013.01); *B28C 5/4244* (2013.01); *F24F 3/0442* (2013.01); *F24F 13/32* (2013.01);
(Continued)

(58) Field of Classification Search
CPC ......... B28C 7/0454; B28C 7/026; B28C 7/16; B28C 7/028; B28C 5/422; B28C 5/4244;
(Continued)

(56) References Cited

U.S. PATENT DOCUMENTS 2,658,731 A 11/1953 Osborne
2,927,731 A 3/1960 Swarthout
(Continued)

FOREIGN PATENT DOCUMENTS

AT 6942 6/2004
AU 5227096 11/1996
(Continued)

OTHER PUBLICATIONS

Thomas, Form PCT/ISA/210, International Search Report for PCT/US2013/064600, dated Mar. 10, 2014, 2 pages.
(Continued)

*Primary Examiner* — Marc C Howell
(74) *Attorney, Agent, or Firm* — Craig K. Leon

(57) ABSTRACT

Disclosed are method and system for treating concrete in mixing drums of delivery vehicles having automated rheology (e.g., slump) monitoring systems programmed to dose fluids into concrete based on the monitored rheology. The present invention takes into account a Revolution-To-Discharge value ("RTD") which reflects drum rotations needed to move concrete towards and through the mixing drum opening from which concrete is discharged, and also takes into consideration a Volume-Per-Revolution-Upon-Discharge ("VPRUD") value which reflects the relation between the rate of discharge and rheology (e.g., slump) of concrete upon discharge. The invention is especially useful for reclaiming concrete in the drum after delivery and can confirm rheology based upon peak (maximum) discharge pressure. The present inventors found surprisingly that discharge pressure readings are useful for recalibrating automated rheology monitoring systems as well as for reporting and/or treating the remainder concrete.

19 Claims, 5 Drawing Sheets

(51) Int. Cl.
*F24F 3/044* (2006.01)
*F24F 13/32* (2006.01)
*G01N 11/00* (2006.01)
*F24S 25/60* (2018.01)

(52) U.S. Cl.
CPC .............. *F24S 25/61* (2018.05); *G01N 11/00* (2013.01); *F24S 2025/601* (2018.05); *G01N 2011/006* (2013.01); *G01N 2011/0046* (2013.01); *Y02B 10/20* (2013.01); *Y02E 10/47* (2013.01)

(58) Field of Classification Search
CPC ................. G01N 33/383; G01N 11/00; G01N 2011/0046; G01N 2011/006
USPC .......................................................... 366/2
See application file for complete search history.

(56) References Cited

U.S. PATENT DOCUMENTS

| | | | |
|---|---|---|---|
| 4,008,093 A | 2/1977 | Kitsuda et al. | |
| 4,318,177 A | 3/1982 | Rapp et al. | |
| 4,356,723 A * | 11/1982 | Fay ........................ | G01N 11/00 73/54.03 |
| 4,544,275 A | 10/1985 | Hudelmaier | |
| 4,900,154 A | 2/1990 | Waitzinger et al. | |
| 4,964,917 A | 10/1990 | Bobrowski et al. | |
| 5,099,688 A | 3/1992 | De Mars | |
| 5,203,919 A | 4/1993 | Bobrowski et al. | |
| 5,427,617 A | 6/1995 | Bobrowski et al. | |
| 5,713,663 A | 2/1998 | Zandberg et al. | |
| 5,752,768 A | 5/1998 | Assh | |
| 6,042,258 A | 3/2000 | Hines | |
| 6,042,259 A | 3/2000 | Hines | |
| 6,123,444 A | 9/2000 | Silbernagel | |
| 6,484,079 B2 | 11/2002 | Bckelew et al. | |
| 6,611,755 B1 | 8/2003 | Coffee et al. | |
| 6,892,131 B2 | 5/2005 | Coffee et al. | |
| 7,489,993 B2 | 2/2009 | Coffee et al. | |
| 7,730,903 B2 | 6/2010 | Lindblom et al. | |
| 8,020,431 B2 | 9/2011 | Cooley et al. | |
| 8,118,473 B2 | 2/2012 | Compton et al. | |
| 2002/0015354 A1 | 2/2002 | Buckelew | |
| 2008/0316856 A1* | 12/2008 | Cooley ................... | B28C 5/422 366/142 |
| 2009/0171595 A1 | 7/2009 | Bonilla | |
| 2010/0312406 A1 | 12/2010 | Cooley et al. | |
| 2011/0029134 A1 | 2/2011 | Hazrati et al. | |
| 2011/0077778 A1 | 3/2011 | Berman | |
| 2011/0320040 A1 | 12/2011 | Koeher et al. | |
| 2012/0016523 A1 | 1/2012 | Koehler et al. | |
| 2012/0020180 A1 | 1/2012 | Koehler et al. | |
| 2012/0204625 A1 | 8/2012 | Beaupre et al. | |
| 2012/0250446 A1 | 10/2012 | Cook et al. | |
| 2013/0145967 A1 | 6/2013 | Koehler et al. | |

FOREIGN PATENT DOCUMENTS

| | | |
|---|---|---|
| EP | 1842643 | 10/2007 |
| EP | 2165815 | 3/2010 |
| GB | 2144240 | 2/1985 |
| GB | 2329027 | 3/1999 |
| GB | 2392502 | 2/2007 |
| GB | 2426347 | 2/2007 |
| WO | 2007060272 | 5/2007 |
| WO | 2009144523 | 3/2009 |
| WO | 2009126138 | 10/2009 |
| WO | 2010111204 | 9/2010 |

OTHER PUBLICATIONS

Thomas, Form PCT/ISA/237, Written Opinion of the International Searching Authority for PCT/US2013/064600, dated Mar. 10, 2014, 5 pages.

* cited by examiner

MONITORING DISCHARGE PRESSURE ON CONCRETE MIX LOAD

This is a divisional application based on Ser. No. 14/052,310, filed Oct. 11, 2013, and allowed, which was based on U.S. Ser. No. 61/713,935 filed Oct. 15, 2012.

FIELD OF THE INVENTION

The present invention relates to manufacturing of concrete, and more particularly to a system and method for treating concrete and/or reporting volume of concrete in a delivery vehicle mixing drum, and especially with regard to concrete remaining in the mixing drum after prior partial discharge or delivery.

BACKGROUND OF THE INVENTION

Bobrowski et al. taught that concrete remaining in the mixing drum of delivery trucks can be reclaimed for use by adding a retarding admixture to stabilize the remainder concrete (See U.S. Pat. No. 4,964,917), optionally adding new concrete to the remainder (See U.S. Pat. No. 5,203,919), and then using an accelerator just before re-using the reclaimed concrete (See U.S. Pat. No. 5,247,617).

Hines et al. taught that the amount of admixture to be dosed into the truck returning from delivery can be calculated based on remaining load size and temperature of the concrete (See U.S. Pat. No. 6,042,258) and that admixture dosing could be done on an automated basis (See U.S. Pat. No. 6,042,259).

The present inventors believe that prior art methods for calculating the concrete load remaining in the truck after delivery are neither sufficiently accurate nor practically convenient. For example, it is known to weigh the mixing truck on a weight scale before and after delivery (See e.g., U.S. Pat. Nos. 5,752,768; 6,123,444; 8,020,431; and GB 2392502), but weight can vary due to imprecision of the scale and various other factors (such as fluctuation of fuel tank and other fluid tank levels).

It is also known to estimate concrete discharged from the drum by counting mixing drum rotations required to discharge a known volume of concrete. A typical concrete mixing drum has a pair of mixing blades mounted on the inner drum wall, helically arrayed about the rotational axis of the drum. The blades thus function in the manner of an Archimedes' screw device. When the drum rotates in the "charge" (loading or mixing) direction, the blades push concrete towards the closed end of the drum; and, when the drum rotates in the "discharge" direction, the blades push concrete towards and through an opening located at the opposite end of the drum. The concrete expelled through the drum opening can then be guided by a chute to the desired spot where it is to be placed. Often, the load will not be fully discharged, and the remainder will be returned in the mixing drum to the plant or moved to another placement location; and the remaining volume of concrete would typically be measured by rough visual approximation or by subtracting a rough estimate of the discharged amount from the amount of the original load.

To this point, the current practice of estimating the remainder load has been premised upon the assumption that the amount of concrete discharged from the drum can be calculated based upon the number of drum rotations required to expel the concrete from the drum. This relation is mentioned in various patents, including U.S. Pat. No. 5,752,768 of Assh (Col. 18, line 40 et seq.), U.S. Pat. No. 8,020,431 of Cooley, and U.S. Pat. No. 8,118,473 of Compton. However, the present inventors believe this assumption is predicated on a the underlying assumption that the number of rotations required to bring concrete to the drum opening is constant from load to load, and further that the amount of discharge for each drum rotation is also constant from load to load.

In U.S. Pat. Nos. 6,611,755, 6,892,131, and 7,489,993, Coffee et al. disclosed that Begin Pour and End Pour events (i.e., charging and discharge) can be based upon, among other approaches, the number of drum rotations in the discharge direction, and that the truck can be weighed as part of determining amounts of concrete remaining in the drum after the End Pour event. The number of discharge revolutions for the Begin Pour event is hitherto assumed or estimated to be 1 or 2 drum revolutions, regardless of the load size of the concrete. While this may be adequate for determining Begin Pour and End Pour events, the present inventors believe that a novel system and method are required for achieving high accuracy in calculating the amount of concrete remaining in the drum after partial discharge.

SUMMARY OF THE INVENTION

In surmounting the disadvantages of the prior art which hitherto attempts to measure the amount of concrete as a static amount presumed to be expelled from the delivery truck concrete mixing drum in a fixed amount per fixed rotation of the drum, the present inventors provide a novel, convenient, and highly accurate method for treating concrete and/or reporting volume of concrete in the mixing drum.

The invention involves a highly accurate determination of the amount of concrete in the mixing drum and takes into account (i) the Revolution-To-Discharge value (RTD) which is the number of drum rotations required to move the concrete load into discharge position, and this is primarily a function of load size; and (ii) the Volume-Per-Revolution-Upon-Discharge value (VPRUD) which reflects the amount of concrete removed per drum revolution after the load begins discharging, and this is primarily a function of concrete rheology (e.g., slump) at discharge. RTD and VPRUD values are illustrated by FIGS. 1 and 2, respectively, and further discussed hereinafter.

The invention is particularly useful for treating concrete remaining in the drum after a portion of the concrete has been discharged, such as when the vehicle has returned from a delivery, or when the vehicle is moved from one pouring event to another pouring event (on another construction site or even at the same site).

An exemplary method of the present invention for treating concrete and/or reporting volume of concrete in a mixing drum comprises: (A) determining load size of concrete remaining in the mixing drum after prior partial discharge of concrete from the drum, by employing an automated rheology monitoring system having a computer processor unit ("CPU"), said CPU being connected to at least one sensor for measuring rheology of concrete in the mixing drum, said CPU being connected to a sensor for determining the number of mixing drum rotations, said CPU being programmed to calculate load size ("LS") based on the following formula: LS=OLS−(RR−RTD)*VPRUD, wherein "OLS" represents the original load size of concrete in the mixing drum before said previous partial discharge of concrete from the drum; "RR" represents the number of drum rotations in the discharge direction required for said previous partial discharge; "RTD" represents the Revolutions-To-Discharge value which corresponds to the number of mixing drum rotations in the discharge direction required to commence discharge of concrete from the mixing drum, the number of mixing drum rotations being a function of OLS; and "VPRUD" represents the Volume-Per-Revolution-Upon-Discharge value which corresponds to discharge rate of the concrete in terms of amount of concrete discharged for each mixing drum rotation in the discharge direction (as the discharge rate of concrete is a function of the rheology of the concrete at the time of discharge); the OLS, RR, RTD, and VPRUD being stored in CPU-accessible location and employed by a CPU in calculating load size of the concrete remaining in the drum after previous partial load discharge; and (B) treating and/or reporting the volume of the concrete remaining in the mixing drum, based on the remaining load size determined in accordance with the formula provided above, said treating and/or reporting comprising (i) adding to said concrete in the mixing drum a fluid comprising water, chemical admixture, or both, the amount of said fluid added determined in respect of said determined concrete load size within the mixing drum; (ii) adding to said concrete in the mixing drum an amount of fresh concrete which is determined in respect of said determined concrete load size within the mixing drum; (iii) reporting the determined concrete load size on an electronic display; (iv) reporting the determined concrete load size to the dispatch center; (v) reporting the determined concrete load size to a customer; or (vi) performing some or all of any of the foregoing (i) through (v).

An exemplary system of the invention for treating concrete and/or reporting volume of concrete in a mixing drum remaining after prior partial discharge, comprises: a computer processing unit (CPU) electrically or wirelessly connected to at least one sensor for measuring rheology of concrete in the mixing drum, at least one sensor (e.g., speed, accelerometer) for measuring the rotational speed of the mixing drum, and a CPU-accessible location having software instructions for the CPU to achieve the steps A and B as previously described above.

In preferred methods and systems of the present invention, slump of the concrete is measured by ascertaining the peak pressure in the discharge port of the hydraulic system that rotates the mixing drum during discharge, and the slump value can be employed in the above-described formula (such as for computing the Volume-Per-Revolution-Upon-Discharge value or "VPRUD"), whereby the concrete volume in the drum is calculated. The present invention provides an accurate and convenient method and system for treating the concrete (e.g., dosing with fluid or further concrete additions) or for reporting concrete volume or other properties. The present inventors have surprisingly discovered that this "peak discharge pressure" provides an accurate indication of the slump of the concrete. This slump (or other rheological) value at discharge can be stored in CPU-accessible memory and used for various purposes, such as for calibrating the correlation data between a data set of rheology values and corresponding data set of fluid dosage additions (water, chemicals) when the mixing drum is rotated in the charge direction (wherein the dosage additions have been correlated with rheology state achieved by adding a given dosage or amount).

For example, if the CPU monitors concrete slump and instructs that a dosage of chemical admixture (e.g., superplasticizer) be added into the mixing drum to increase the slump to a target slump desired at final delivery (pour), the automated concrete monitoring system can monitor the peak discharge pressure and compare this to prior correlations (i.e., in CPU-accessible memory or storage) between peak discharge pressure values previously measured (using sensor for measuring the hydraulic pressure to rotate drum in discharge direction) and discharged-concrete slump values previously measured (using a standard slump cone); and the CPU can be programmed to recalibrate the automated rheology monitoring system wherein slump is monitored by sensing rotation of the drum in the charge (mixing) direction and chemical admixture is dosed into the drum during mixing to reach a desired slump level.

An exemplary method of the present invention for monitoring rheology of concrete, comprises: in an automated concrete rheology monitoring system having a computer processing unit (CPU) connected electrically or wirelessly to a plurality of sensors configured for monitoring conditions on a concrete delivery vehicle having a mixing drum for concrete, including a sensor for monitoring discharge pressure on the mixing drum, performing the following steps: monitoring discharge pressure of a concrete load discharged from the concrete mixing drum; comparing the monitored peak discharge pressure of the discharged concrete load with CPU-accessible database wherein peak discharge pressure values correspond to concrete rheology values; and reporting a rheology value of the concrete discharged based on the peak discharge pressure as monitored. Preferably, the rotational speed of the drum is monitored, and preferably kept between 1-5 revolutions per minute at discharge.

The reporting step may comprise one or more of the following: (a) indicating said rheology value on a monitor screen and/or ticket; (b) providing an indication on a monitor screen and/or ticket confirming whether or not peak discharge pressure monitored corresponds to a rheology condition that coincides with target rheology specified for the concrete; or (c) performing (a) and (b).

The peak discharge pressure monitored for the discharge load can be used in the calculation of remaining load size (LS), in accordance with the above-described formula, LS=OLS−(RR−RTD)*VPRUD, wherein "OLS" represents the original load size of concrete in the mixing drum before said previous partial discharge of concrete from the drum; "RR" represents the number of drum rotations in the discharge direction required for said previous partial discharge; "RTD" represents the Revolution-To-Discharge value which corresponds to the number of mixing drum rotations in the discharge direction required to commence discharge of concrete from the mixing drum, said number of mixing drum rotations being a function of concrete load size in the mixing drum; and "VPRUD" represents the Volume-Per-Revolution-Upon-Discharge value which corresponds to discharge rate of the concrete in terms of amount of concrete discharged for each mixing drum rotation in the discharge direction, said discharge rate of concrete being a function of the rheology of the concrete at the time of discharge; and said OLS, RR, RTD, and VPRUD being stored in CPU-accessible location and employed by a CPU in calculating load size of the concrete remaining in the drum after a prior partial discharge.

An exemplary system of the present invention for monitoring concrete in a delivery vehicle mixing drum comprises: an automated concrete rheology monitoring system having a computer processing unit (CPU) connected electrically or wirelessly to a plurality of sensors for monitoring conditions on a concrete delivery vehicle having a mixing drum, including sensor for monitoring charge pressure, sensor for monitoring discharge pressure, and sensor for monitoring rotational speed of the mixing drum; a set of CPU-accessible correlation values wherein peak discharge pressure is correlated with rheology of concrete discharged;

and instructions for the CPU to monitor discharge pressure for rotating the mixing drum in the discharge direction and for reporting a rheology value of the concrete discharged from the mixing drum based on the peak discharge pressure as monitored.

For example, reporting can be performed by having the system transmit, such as to the dispatch center or customer, data to confirm the slump of the concrete at discharge, or to initiate an alarm if the concrete slump as monitored at discharge (using the peak pressure value) is found by the system to differ from the target slump that was previously specified for delivery. If slump at delivery has been found by the system to depart from the target slump specified by the customer by 10%, 15%, 20% or more, the system can alert the ready-mix producer, the driver, the dispatch center (if different from the ready-mix plant), and/or the ready-mix customer of this fact, so that corrective steps can be taken if necessary or the load can be returned if corrective steps cannot be taken to restore the concrete to the target rheology condition specified by the ready-mix producer or customer.

The present inventors further discovered that discharge pressure monitoring is useful for confirming when concrete has been completely unloaded from the mixing drum. Thus, an exemplary method for determining when discharge of concrete from a delivery vehicle mixing drum is complete, comprises: monitoring discharge pressure for rotating the mixing drum in the direction of discharge, by employing a sensor which is in electrical or wireless combination with an automated concrete monitoring system having a computer processing unit (CPU); sensing when discharge pressure falls below a predetermined discharge pressure value stored into CPU-accessible memory or storage, the predetermined discharge pressure value corresponding with an empty mixing drum state; and reporting completion of the concrete discharge from the mixing drum. For example, where the rotation rate of the drum in discharge direction is 2-5 revolutions per minute (RPM), the predetermined discharge pressure value is preferably between 100-400 RPM, and more preferably between 150-250 RPM.

The above-described methods and systems of the invention therefore provide surprising new capabilities for the concrete industry to monitor and to ensure consistency and high quality in the concrete being delivered to the customer.

Further advantages and features may be discussed hereinafter.

BRIEF DESCRIPTION OF THE DRAWINGS

Further advantages and features of the present invention may be more readily comprehended when the following detailed description of preferred embodiments is considered in conjunction with appended drawings wherein.

DETAILED DESCRIPTION OF EXEMPLARY EMBODIMENTS

Figure 1:
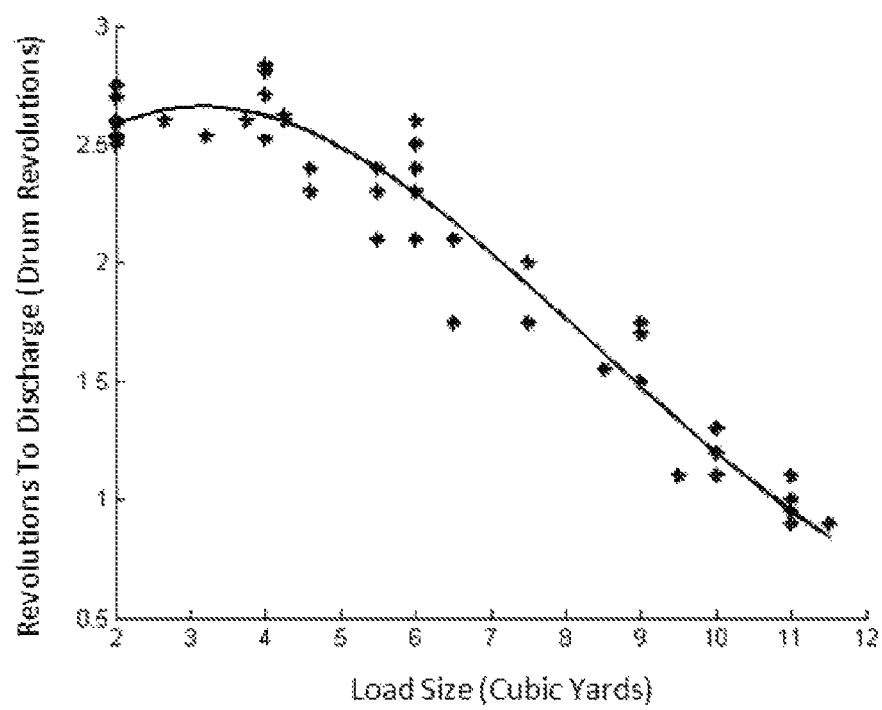
FIG. 1 is a graphic illustration of a "Revolution-To-Discharge" (RTD) value which the inventors deem to indicate the number of mixing drum revolutions, as a function of load size, needed for commencing concrete discharge from the delivery truck mixing drum opening.

The term "concrete" as used herein will be understood to refer to materials including a cement binder (e.g., Portland cement optionally with supplemental cementitious materials such as fly ash, granulated blast furnace slag, limestone, or other pozzolanic materials), water, and aggregates (e.g., sand, crushed gravel or stones, and mixtures thereof), which are effective for forming a building or civil engineering structure when in a hardened state. The concrete optionally contains one or more chemical admixtures, such as plasticizing admixtures (including water-reducing agents, such as lignosulfonates, or superplasticizers (e.g., polycarboxylate comb polymers), set retarders, set accelerators, air entrainers, air detrainers, strength enhancers, pigments, colorants, fibers for plastic shrinkage control or structural reinforcement, and the like.

Conventional chemical admixtures are contemplated for use in the present invention. When incorporated into left over or remainder concrete which is deemed suitable for re-use, such an admixture is sometimes referred to as a "stabilizing" or "hydration stabilizing" or "hydration controlling" admixture. Such admixtures can include set retarders, water-reducers, agent, or mixture of these. Lignosulfonates, for example, are water-reducers having retarding characteristics.

A stabilizing admixture in the form of a ready-to-use aqueous solution is available from Grace Construction Products, Massachusetts, USA, under the RECOVER® trade name. This is often used as a stabilizing admixture for left over concrete and is believed to be suitable for purposes of the invention.

As mentioned in the background section, ready-mix delivery trucks typically have a pair of mixing blades mounted on the inner wall of the mixing drum, and somewhat helically arrayed around the rotational axis of the drum. The blades act in screw-like fashion to push concrete towards the closed end of the drum when rotated in the "charge" (or loading-mixing) direction; the blades otherwise push concrete towards and through an opening at the opposite end of the drum when it rotated in a "discharge" direction. The rotational axis of the mixing drum is usually slanted with respect to level ground, such that the opening of the drum, which usually overlaps the rotational axis of the drum, is located at a somewhat higher level than the closed end, such that the blades must push the concrete upwards against the inclined inner wall of the rotating drum towards the opening through which the concrete is expelled. The principles of the present invention may be applied to ready-mix trucks which have more or fewer blades, but trucks having two blades appear are the most prevalent in the industry. In any event, concrete delivery vehicles having rotatable mixing drums with the above-described orientation of mixing blades are contemplated for use in the present invention.

The mixing drums for ready mixed concrete trucks are rotated by a hydraulic pump and motor. The pump is connected to the PTO of the engine of the vehicle and the motor is connected to the mixing drum. In order to operate the drum in either the charge or discharge direction, the hydraulic motor is connected to the chambers associated with charge and with discharge. Test ports are typically available for mounting pressure sensors for monitoring hydraulic pressure on both the charge and discharge side. Generally, when the mixing drum is rotated in the charge direction, the pressure of the hydraulic fluid in the charge port increases. When the mixing drum is rotated in the discharge direction, pressure of the hydraulic fluid in the discharge side of the motor increases. The present invention involves mounting sensors for monitoring pressure on the charge port ("charge pressure") and sensors for monitoring pressure on the discharge port ("discharge pressure").

Concrete trucks are commonly equipped with water tanks connected by a hose line directed into the drum opening. In this manner, fluid can be dispensed into the drum under air pressure in the tank or by pump. Such tank dispensing devices are disclosed in U.S. Pat. Nos. 4,544,275, 7,842,096 and U.S. patent application Ser. No. 11/955,737, for example. When a chemical admixture tank is the fluid conveyed on the truck, the tank is typically connected to the same hose line used for discharging water into the drum. The chemical admixture may be dispensed into the water line under air pressure or by tank to the pump. This is exemplified in U.S. Pat. No. 7,730,903. Alternatively, chemical admixtures and water may be dispensed using different lines into the mixing drum.

The terms "rheology" as used herein is intended to include slump, slump flow, DIN flow, yield stress, thixotropy, and other rheological characteristics of plastic concrete. "Slump" is used herein as a matter of convenience, as systems for monitoring concrete slump are becoming recognized in the industry, wherein the force or energy required to rotate the concrete drum (such as hydraulic pressure) is correlated with slump of the concrete in the drum (whereby slump is measured by using a standard slump cone test for a given sample of concrete), and the effects of water and chemical admixture, respectively, on the concrete slump can also be monitored and the relationship stored in computer memory for later use in adjusting or controlling the slump of the concrete by administering the dose as determined by the computer processing unit.

These relationships are described by some of the references as may be various described herein. It is thus possible that other rheological properties of the concrete, other than or in addition to slump, can be correlated with pressure and/or other forces required to rotate the drum; although "slump" and "pressure" (hydraulic) will be used as the most convenient concepts for explication of the present invention.

For example, automated concrete slump monitoring systems on concrete delivery vehicles (e.g., ready mix trucks) are disclosed in U.S. Pat. Nos. 6,611,755; 6,892,131; and 7,489,993 of Coffee et al. (owned by the common assignee hereof) may be suitable for modified use in the present invention. Other exemplary automated concrete slump monitoring systems are believed to be suitable for modified use in the present invention, such as U.S. Pat. No. 6,484,079 and Ser. No. 09/845,660 of Buckelew. These references are again incorporated herein by reference.

In particular, Buckelew disclosed providing a sensor in the hydraulic line for rotating the truck mixing drum in the charging direction, as well as a separate sensor in the hydraulic line for rotating the truck mixing drum in the discharging direction.

The term "charge pressure" will be used herein to refer to the (hydraulic) pressure in the pump-motor hydraulic system to rotate the mixing drum in the loading/charging/mixing direction; while "discharge pressure" will be used herein to refer to refer to the (hydraulic) pressure in the pump-motor hydraulic system to rotate the drum in the direction to discharge or expel concrete from the drum.

It is believed that a number of exemplary embodiments of the invention may be practiced using commercially available automated concrete mix monitoring equipment with modifications as would be apparent in view of the teachings disclosed herein. Automated slump monitoring systems are available from Verifi LLC, West Chester, Ohio, and Cambridge, Mass., USA, under the trade name VERIFI®, and these are believed to be suitable for modification in accordance with the teachings of the present invention as disclosed herein.

The term "automated slump monitoring system" will be used to refer to computer processor unit (CPU) devices which are effective for monitoring at least one rheological property of concrete in mixing drums. This is accomplished by measuring hydraulic, electrical, or other forces required for rotating the mixing drum, and for correlating the measured force value with the slump/rheological value; and optionally for dispensing water or chemical additives to adjust or to control the slump/rheological value.

As summarized above, an exemplary method of the present invention for treating concrete and/or reporting volume of the concrete in a mixing drum, such as concrete remaining after prior partial discharge of concrete from the drum, comprises two basic steps, which are labeled "A" and "B" which are further described below:

Step (A) involves determining load size of concrete, and this methodology is applicable to determination of concrete remaining in the mixing drum after delivery or any other prior partial discharge of concrete from the drum. This load size (LS) can be computed by subtracting, from the number of drum rotations in the discharge direction required for expelling or discharging the concrete from the drum, the "Revolutions-To-Discharge" value, which is the number of drum rotations in the discharge direction required for moving the concrete material up to the drum opening, and then multiplying this difference by the "Volume-Per-Revolution-Upon-Discharge value," which corresponds to the rate of concrete discharged for each drum rotation in the discharge direction as a function of rheology (e.g., slump) at the time of discharge. This amount of concrete discharged is subtracted from the original load size (OLS) that was loaded into the mixing drum at the batch plant.

The above calculation is preferably accomplished by use of an automated rheology (e.g., slump) monitoring system having a computer processor unit ("CPU") wherein the CPU is connected to at least one sensor for measuring rheology (e.g., slump) of the concrete in the mixing drum, and the CPU is connected to a sensor for determining the number of mixing drum rotations, and the CPU is programmed to calculate remainder load size ("LS") based on the following formula:

$$LS = OLS - (RR - RTD) * VPRUD$$

wherein "OLS" represents the original load size of concrete in the mixing drum before said previous partial discharge of concrete from the drum (wherein OLS may be inputted at the batch plant, either manually by the batch plant manager, or electronically by the automated batching system); "RR" represents the number of drum rotations in the discharge direction required for the previous partial discharge of concrete from the mixing drum; "RTD" represents the Revolution-To-Discharge value which corresponds to the number of mixing drum rotations in the discharge direction required to commence discharge of concrete from the mixing drum, the number of mixing drum rotations being a function of concrete load size in the mixing drum; and "VPRUD" represents the Volume-Per-Revolution-Upon-Discharge value which corresponds to discharge rate of the concrete in terms of amount of concrete discharged for each mixing drum rotation in the discharge direction, the discharge rate of concrete being a function of the slump of the concrete at the time of discharge; and each of the OLS, RR, RTD, and VPRUD values are stored in CPU-accessible location (e.g., memory or storage file on the truck or located at a remote location) and employed by CPU in calculating load size of the concrete remaining in the drum after previous partial load discharge.

Step "B" involves treating the concrete and/or reporting a volume of the concrete contained in the mixing drum (or otherwise remaining in the drum after a partial discharge or after delivery) based on the calculation done in Step (A), wherein remaining load size is determined based on LS=OLS−(RR−RTD)*VPRUD as set forth above, and the exemplary treating step comprises: (i) adding to said concrete in the mixing drum a fluid comprising water, chemical admixture, or both, the fluid added being in an amount determined in respect of said determined concrete load size; (ii) adding to the concrete in the mixing drum an amount of fresh concrete which is determined in respect of the determined concrete load size within the mixing drum; (iii) reporting said determined concrete load size on an electronic display; (iv) reporting the determined concrete load size to dispatch center; (v) reporting the determined concrete load size to a customer; or (vi) performing some or all of any of the foregoing (i) through (v).

For example, if step B(i) is pursued, the monitoring system CPU can be programmed to add a predetermined amount of cement dispersant admixture (e.g., superplasticizer) into the mixing drum based on the remaining load size as calculated in step (A). Accordingly, the system CPU can be programmed to access a database wherein admixture amounts have been previously correlated with rheology changes, such that an appropriate amount of admixture can be added into the mixing drum such that the concrete can be treated so as to obtain a desired or target rheology (e.g., slump). Automated slump monitoring systems may, for example, be programmed by inputting the desired or target rheology into the CPU.

As another example, if B(ii) is selected and the remainder concrete is deemed to be suitable for re-cycling, then the remainder amount can be determined in accordance with step (A) and a supplemental concrete can be added up to a predetermined or desired new load amount.

As a further example, if B(iii) is selected, the monitoring system CPU can be instructed to report the remainder amount of concrete in the mixing drum as calculated in step (A), such as by transmitting an indication or value corresponding to the remainder amount and/or the calculated prior discharged amount to a monitor screen of a personal computer, laptop, or hand-held device in possession of the ready-mix producer or dispatch center, the customer, architect, or person located at a remote location. A person working in the dispatch center could, for example, determine whether any remaining concrete is suitable for use on a different construction site.

A system for treating concrete and/or reporting volume of concrete in a mixing drum remaining after prior partial discharge, comprising: a computer processing unit (CPU) electrically or wirelessly connected to at least one sensor for measuring rheology of concrete in the mixing drum, at least one sensor (e.g., speed, accelerometer) for measuring the rotational speed of the mixing drum, and a CPU-accessible location having software instructions for the CPU to achieve steps A and B, as previously set forth above. In preferred embodiments, the CPU is electrically or wirelessly connected to at least one sensor for measuring the (hydraulic) pressure for rotating a concrete mixing drum in the charge direction, and at least one sensor for measuring the (hydraulic) pressure for rotating the concrete mixing drum in the discharge direction.

Once the remainder concrete amount is calculated in step (A) and the concrete is treated and/or reported as provided in step (B), further exemplary methods and systems of the invention can further comprise determinations by the system CPU, based on the remainder concrete slump, temperature, and batch mixture components, other jobsites where the remainder concrete can be utilized. The temperature of the concrete in the mixing drum can be monitored, and the information regarding the batch components can be either inputted at the batch plant and/or automatically downloaded from the batching system at the plant.

Figure 2:
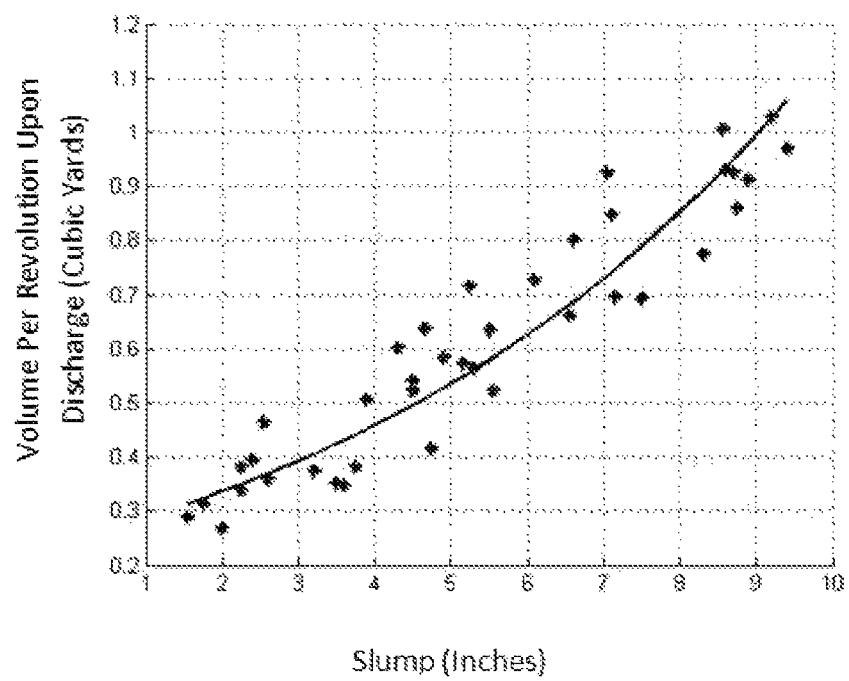
FIG. 2 is a graphic illustration of a "Volume-Per-Revolution-Upon-Discharge" (VPRUD) value which the inventors deem to indicate the rate of concrete discharge, in terms of cubic yards of concrete for each revolution of the mixing drum, as a function of the concrete slump at the time of discharge from the mixing drum, wherein slump of discharged concrete is measured in inches.

Also as summarized previously, the calculation of remainder concrete amount involves consideration in step (A) of the RTD value, an example of which is provided in FIG. 1, and the VPRUD value, an example of which is provided in FIG. 2. The drawings in FIGS. 1 and 2 are discussed in further detail as follows.

In FIG. 1, the Revolution-To-Discharge value (RTD) suggests the delay factor and is expressed in terms of the number of drum rotations required for a particular concrete load size to be pushed by the mixing blades upwards along the inner drum wall and towards the drum opening through which the concrete is expelled (discharged) from the mixing drum. In other words, the RTD value is the number of rotations needed to start removing concrete material from the mixing drum. No concrete comes out of the mixing drum until this number of revolutions is reached. Hence, the RTD value is a function of load size.

In FIG. 2, the "Volume-Per-Revolution-Upon-Discharge" (VPRUD) value is used to determine how much concrete volume comes out of the drum when the drum is rotated in the discharge direction. In this situation, the present inventors discovered that the rate at which the concrete is discharged is a function primarily of the slump of the concrete (with some effect from the geometry or shape of the drum which contains the concrete) at the time of discharge.

By subtracting the RTD value from the number of discharge revolutions (RR) and multiplying this difference by the VPRUD value, the present inventors surprisingly discovered that they could accurately determine the amount of concrete discharged from the drum. When the volume of discharged concrete was predicted based on the foregoing calculations, the present inventors found that their predictions were highly accurate when compared to data points obtained empirically using concrete discharged with known slump as measured by standard slump cone. Hence, the predicted discharge volumes per drum rotation are compared to actual discharge volumes per drum rotation, and these values are illustrated in FIG. 3.

Figure 3:
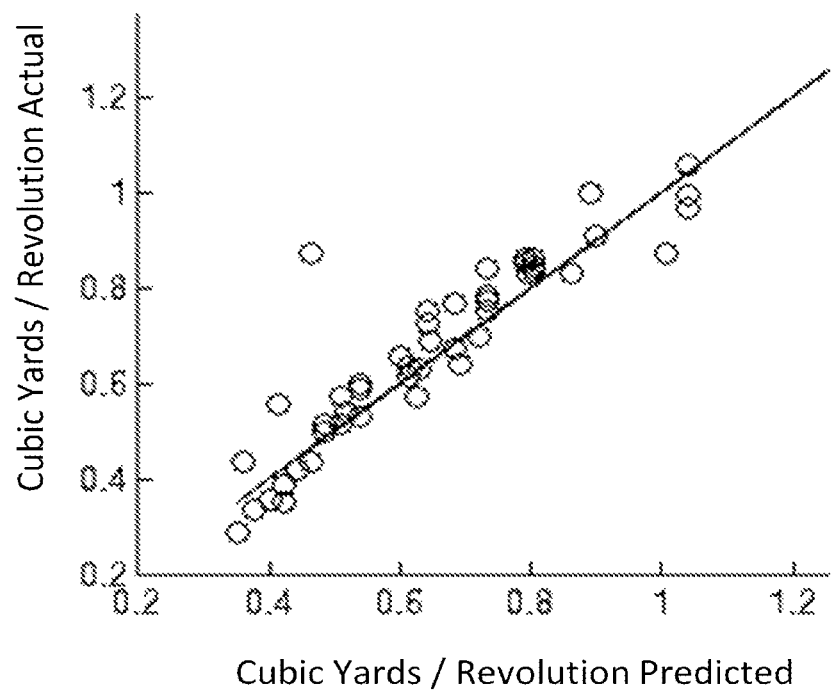
FIG. 3 is graphic illustration of actual volume of concrete discharged per drum revolution compared to predicted volume of concrete discharged per drum revolution.

FIG. 3 confirms the high accuracy afforded by the present invention in terms of the ability to calculate the volume of unloaded concrete, and, hence, the volume of concrete remaining in the mixing drum.

The present inventors discovered that monitoring the discharge pressure provides an indication of when the concrete is completely discharged from the drum (as will be further discussed hereinafter), but more significantly reveals a surprising and unexpected property of the concrete during its last moments in the mixing drum. As mentioned above, the "discharge pressure" value can be measured from a sensor installed in the hydraulic line used for forcing the drum to rotate in a discharge direction; this is different from the sensor installed in a line for hydraulically forcing rotation of the drum in the charging/mixing direction. The present inventors discovered that there is a correlation between peak (or maximum) discharge pressure and the slump of the discharged concrete, and that this correlation exists independent of the size of the load being discharged. This surprising discovery occurred when the inventors examined the data illustrated in FIGS. 4A-4C and 5.

Figure 4A:
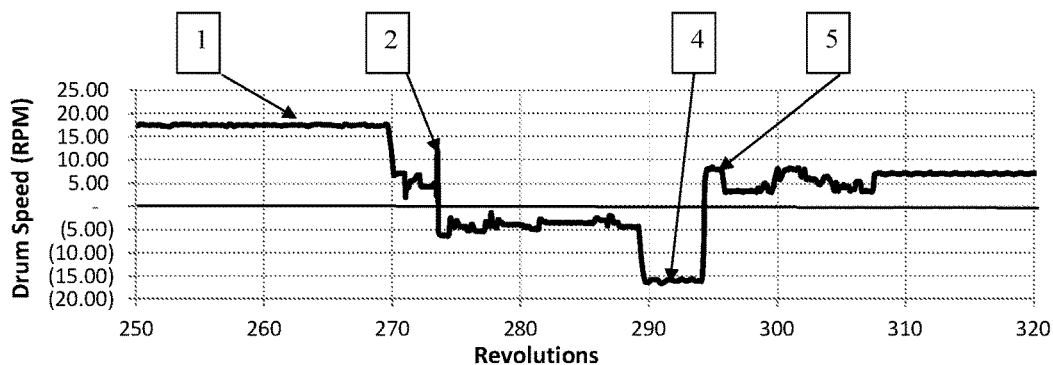
FIGS. 4A, 4B, and 4C are graphic illustrations of a concrete mix during loading and unloading, whereby each of the respective properties of drum rotation speed in both directions of loading and unloading (See FIG. 4A), charge pressure (See FIG. 4B), and discharge pressure (See FIG. 4C) are plotted along their respective vertical axes as a function of mixing drum rotations as plotted along the horizontal axis.
Figure 4B:
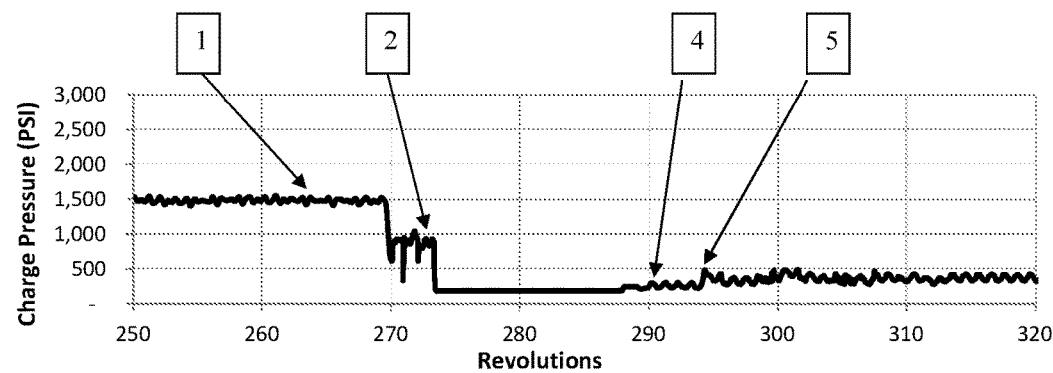
Figure 4C:
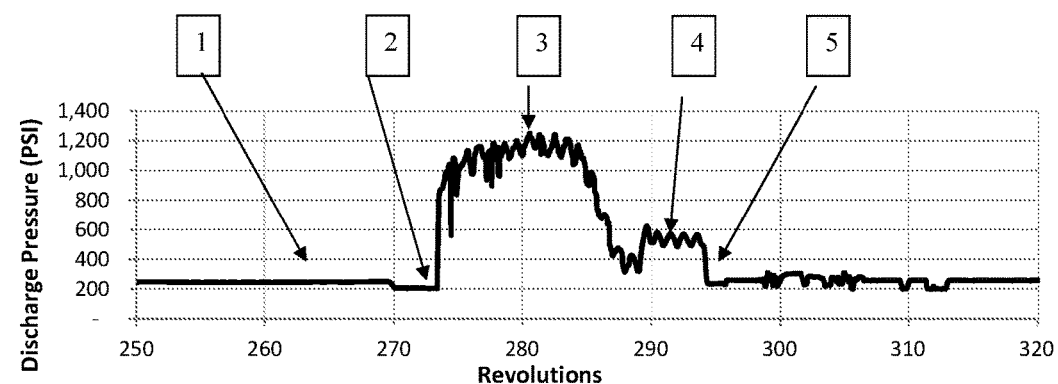

FIGS. 4A, 4B, and 4C each graphically illustrate, for the same concrete loading and unloading operation on a delivery truck, the drum speed and rotational direction with respect to drum speed (See FIG. 4A), the charge pressure (See FIG. 4B), and the discharge pressure (See FIG. 4C), each as a function of drum rotation as indicated along the horizontal axis of each of the respective graphs in FIGS. 4A-4C, which are arranged to represent states during loading and discharge.

The rotational speed of the mixing drum is indicated in FIG. 4A along the left vertical axis in terms of revolutions per minute ("RPM") in increments of 5 RPM, and this is provided for the charging direction as shown in the upper half (positive value) of FIG. 4A as well as for the discharging direction as shown in the lower half (negative value) of FIG. 4A. As indicated at 1 in FIG. 4A, the mixing drum is in charging mode, as concrete is loaded and mixed, and drum speed is held constant at about 17 RPM. As indicated for this same period in FIG. 4B, the charge pressure is high (about 1,500 PSI); while for this same period in FIG. 4C, the discharge pressure is low (about 225 PSI).

As shown at 2 in FIG. 4A, the mixing drum reverses direction and goes into discharge mode (approximately by 273$^{rd}$ drum revolution). During discharge mode between the 273$^{rd}$ and 289$^{th}$ drum revolution, the drum speed is nearly constant (about 4.6-5.2 RPM) as indicated by the relatively flat portion of the graph. During this phase, the charge pressure drops to a very low point as shown in FIG. 4B; while the discharge pressure climbs very rapidly as shown in FIG. 4C.

Peak discharge pressure is designated at 3 in FIG. 4C. As will be further explained hereinafter, the present inventors were surprised to find that this peak or maximum discharge pressure reflected a consistent relationship with rheology (e.g., slump) of the concrete being discharged from the mixing drum. This relationship is best seen when the rotational speed of the discharging mixing drum is kept as constant as possible, such as between 1 and 5 or 6 revolutions per minute.

By the 285$^{th}$ rotation, discharge pressure begins to decrease rapidly (as shown in FIG. 4C). At the 289$^{th}$ rotation, drum speed and discharge pressure are increased as the last remaining concrete is expelled from the drum. The mixing drum can then be returned to the plant for the next load and set into charge mode for this purpose (as shown at 5 in FIG. 4A).

It is further evident from FIG. 4 that drum speed has an effect on both discharge and charge pressure, even when the rheology and load size are not changing. Thus, a sensor for measuring drum speed can be provided.

Figure 5:
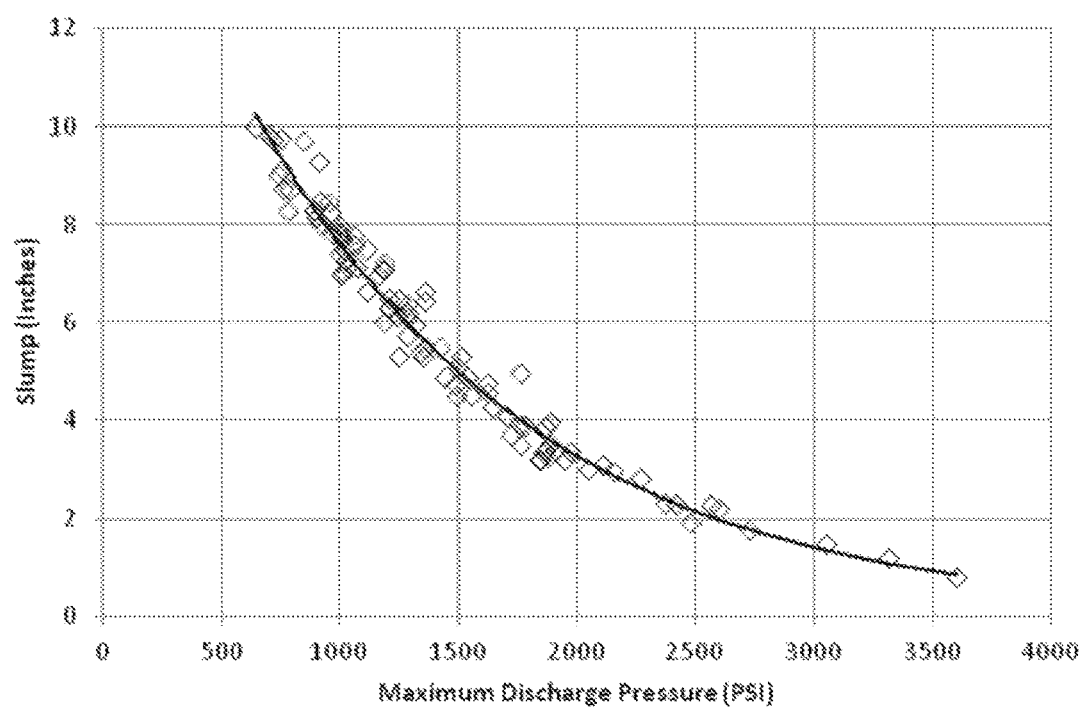
FIG. 5 is a graphic illustration of a correlation between slump of concrete (inches) and the maximum (peak) discharge pressure (pounds per square inch) for rotating the mixing drum in the discharge direction.

FIG. 5 illustrates graphically the correlation that was surprising discovered by the present inventors between the peak (maximum point) of discharge pressure and the slump of the discharged concrete. The rotation speed of the drum in discharge mode should preferably be kept constant between 1-6 RPM, and, more preferably, about 2-4 RPM for optimum results. The results in FIG. 5 were based on data obtained from 97 deliveries using three different fleets of concrete mixing trucks having automated slump monitoring systems, and these results demonstrate a relationship hitherto unknown in the industry. It was unexpected and surprising that this relationship can be used to determine what the slump of concrete was at discharge by measuring peak pressure during discharge of the concrete.

In view of this discovery, the inventors set forth other aspects of their invention as follows.

In exemplary methods and systems of the invention, the rheology of concrete discharged from mixing drum is determined based on peak discharge pressure and the drum rotation speed as measured during discharge of concrete from the drum. The automatic rheology (e.g., slump) monitoring system CPU can be programmed with instructions or to access a database containing (prior) correlations between values of peak discharge pressure and rheology (slump) values (as graphically illustrated for example in FIG. 5), and the peak discharge pressure for a given load is then measured (at known constant drum rotation speed in discharge direction). The CPU is also programmed to issue a report, for example, in the form of an alarm (such as where slump measured at discharge differs substantially by a predetermined difference value from the target slump that was previously specified into the system CPU for discharge). For example, the predetermined difference value may be 5%, 10%, 15%, 20%, 25%, or more, which may be set as desired by the ready-mix producer or by the dispatch center.

An exemplary method of the invention for determining rheology of concrete, comprises: in an automated concrete rheology monitoring system having a computer processing unit (CPU) connected electrically or wirelessly to a plurality of sensors configured for monitoring conditions on a concrete delivery vehicle having a mixing drum for concrete, including sensors for monitoring charge pressure and discharge pressure on the mixing drum, performing the following steps: in an automated concrete rheology monitoring system having a computer processing unit (CPU) connected electrically or wirelessly to a plurality of sensors configured for monitoring conditions on a concrete delivery vehicle having a mixing drum for concrete, including a sensor for monitoring discharge pressure on the mixing drum (and optionally and preferably also including sensor for monitoring charge pressure and sensor for measuring rotational speed of the mixing drum), performing the following steps: monitoring discharge pressure of a concrete load discharged from the concrete mixing drum; comparing the monitored peak discharge pressure of the discharged concrete load with CPU-accessible database wherein peak discharge pressure values correspond to concrete rheology values; and reporting a rheology value of the concrete discharged based on the peak discharge pressure as monitored.

The reporting can comprise one or more of the following steps: (a) indicating the rheology value on a ticket and/or monitor screen (of a personal computer, laptop, or hand-held device); (b) providing an indication on a monitor screen and/or ticket confirming whether or not peak discharge pressure monitored corresponds to a rheology condition that coincides with target rheology specified for the concrete; or (c) performing both steps (a) and (b).

The reporting can also additionally include an alarm which is activated on the truck and/or at the dispatch center, if the slump at delivery pour is confirmed, using measurement of peak discharge pressure and comparing the corresponding rheology (slump data), to exceed (by a predetermined amount or percentage) a target slump that was earlier specified by input into the system CPU.

As mentioned in the summary section, the system (apparatus or device) could be installed on a ready-mix concrete delivery truck in the form of commercially available automated slump monitoring system (e.g., VERIFI® control systems) modified in accordance with the teachings of the present invention. CPU-accessible correlation values, wherein peak discharge pressure is correlated with slump of concrete discharged, can be kept in CPU-accessible memory or storage, either located on the truck, or at a remote location (such as dispatch center).

In view of the teachings herein, the system may be modified to report remainder concrete amounts (if any) and/or the rheology of the concrete at discharge, using values or symbols on a monitor screen, such as that of a personal computer, laptop, or hand-held device (e.g., Apple® IPhone® or IPad® devices) to display slump or other rheology property of the concrete as discharged from the mixing drum, or to display the remainder amount of concrete. Such monitor screen can be accessible to the customer as well as to the ready-mix producer.

Other exemplary methods and systems of the invention can be configured such that, based on the use of the CPU-accessible correlation values wherein peak discharge pressure is correlated with slump or other rheology property of the concrete discharged, as well as the use of the above-described method for determining the amount of concrete discharged from the mixing drum, namely, the calculation of concrete discharged using the formula (RR−RTD)*VPRUD (wherein the VPRUD factor can be computed based on peak discharge pressure as monitored (and correlated with a slump value), and calculating remaining concrete load by subtracting the discharged amount from the original load size, it is possible to generate a report regarding volume and/or rheology condition of the concrete, such as through the issuance of a ticket (paper document) or a readout display on a portable electronic screen, regarding amount of concrete delivery (discharged) and slump of concrete at the time of delivery.

Due to the accuracy of using peak discharge pressure monitoring to measure rheology of the concrete, as suggested by the curve in FIG. 3 (which compares actual volume of concrete discharged per drum revolution and predicted volumes of concrete discharged per drum revolution), the present inventors believe it is possible to confirm accuracy of and even to recalibrate an automated rheology (e.g., slump) monitoring system.

Thus, a further exemplary automated concrete rheology monitoring system or method of the invention, wherein said automated concrete rheology monitoring system further comprises CPU-accessible data comprising correlation values between concrete rheology measured prior to discharge based on charge pressure and during discharge based on discharge pressure, and determining whether to update the correlation value involving charge pressure and concrete rheology if the two said concrete rheology values differ by more than a pre-determined amount.

Still further exemplary embodiments comprise using CPU-accessible data having correlation values between concrete rheology and fluid additions which are added into the concrete mix to alter said rheology, and wherein peak discharge pressure is measured and used to calibrate the correlation values between concrete rheology (as monitored by the system based on charge pressure when the drum is rotating in the mixing/loading direction) and the fluid additions which are added into the concrete mix to alter the rheology of the concrete (and the effect of such fluid additions are correlated with rheology as monitored by the system based on charge pressure when the drum is rotating in the mixing/loading direction).

The aforementioned methods and systems of the invention, in view of the foregoing description of advantages and features, can be employed to accomplish a number of functionalities and to provide visual indications (in the form of tickets or larger printouts or monitored displays) confirming that a particular function has occurred or confirming the extent to which it has occurred. For example, exemplary methods and systems can be modified for various beneficial uses, including the following:

(a) As described above, one can use remaining load size to calculate slump; or, conversely, calculate remaining load size or discharged amount based on peak discharge pressure, by having the CPU perform calculations based on stored CPU-accessible correlation values wherein peak discharge pressure is correlated with slump of concrete discharged.

(b) The Revolution-To-Discharge value (RTD) or Volume-Per-Revolution-Upon-Discharge value (VPRUD) as discussed above can be used to confirm the initial load size received in the mixing truck from the batch plant. Thus, for a complete discharge, the CPU should calculate the load size discharged based on (RR−RTD)*VPRUD; and this should be equal to the original load size (OLS) as indicated on a batching ticket or data transmission from the concrete batching plant. Thus, methods and systems of the invention can provide an indication, in the form of a ticket or data transmission to a monitor screen, that the total amount of concrete delivered equaled the original load size.

(c) Calculation of the remaining load size may be used to calculate and/or manage the amount of water or chemical admixture to be added to the concrete in the mixing drum, and such admixtures may include one or more of any, some, or all of the following: water-reducer (e.g., superplasticizer) admixture, set retarding admixture, accelerator admixture), air entraining admixture.

(d) The CPU can be instructed such that alarms, monitor screen symbols, alerts, or other indications can be transmitted, such as by wireless communication, to the dispatch center, the foreman at the construction site, supervisory architect, the driver of the truck or other trucks, etc., that concrete is available (e.g., remaining) in the mixing drum, the volume as well as the slump of the available or remaining concrete.

(e) The CPU can be instructed to provide a separate ticket (paper or electronic) from dispatch software which confirms the remaining quantity of concrete.

(f) The CPU can also be instructed to issue an invoice (paper or electronic) to the customer for disposal of returned concrete (i.e., remainder concrete left over in the truck after return from delivery).

(g) The CPU can also be instructed to determine whether remainder concrete can be re-used based on one or more of the following factors taken into consideration by the CPU: the time since initial batching or loading at the concrete plant, the number of drum revolutions the initial batching or loading, temperature of concrete, quantity of water added to concrete, quantity and type of chemical admixture added to the concrete, the design strength of the concrete, the water-to-cement ratio, and other factors.

(h) Where it is determined that the remainder concrete is suitable for re-use, the CPU can be programmed to calculating the quantity of one or more of cement, sand, coarse aggregate, water, and admixture to be added to the remainder to obtain a second batch of concrete which meets desired slump and compressive strength targets.

(i) The CPU in the automated slump monitoring system can also be programmed to measure or estimate one or more properties, including air content, unit weight, water added to the drum after batching, and using this information to revise the computation of original load size, calculated discharge amounts, and/or calculated remainder amounts after partial discharge. This can be accomplished by providing a means for user to input manually an air content or unit weight test result, or an automated means of measuring air content such as those known in the art.

(j) The CPU can be programmed such that remaining concrete, if a selected minimum load size is detected, and the current slump is detected as being too high, to provide an audible and/or visual alarm so that the driver knows that there is a risk that transporting the load could give rise to sloshing and hence spillage of concrete from the drum.

(k) The CPU can be programmed to determine the relationship between slump, load size, hydraulic pressure, and drum rotation speed for load sizes different from those used in the original calibration, wherein a rate of slump change from begin to end of loading is selected from −1 in to 0 in. per minute.

(l) The systems and methods of the present invention can be calibrated by using a load cell mounted on one or more trucks of substantially similar geometry; or, conversely, the present invention can be used to check the accuracy of load cells that are currently in use.

(m) As explained elsewhere in this specification, the present inventors believe that slump can be replaced with other rheological values including slump flow, DIN flow, or others, such that the calculation of Remaining Load Size (LS) can be calculated based on the LS−(RR−RTD)*VPRUD wherein the Volume-Per-Revolution-Upon-Discharge value (VPRUD) is based on discharge rate as a function of the rheology value at the time of discharge.

Other exemplary methods of the present invention for determining rheology (e.g., slump) of concrete comprise: in an automated concrete rheology monitoring system having a computer processing unit (CPU) connected electrically or wirelessly to a plurality of sensors configured for monitoring conditions on a concrete delivery vehicle having a mixing drum for concrete, including sensors for monitoring charge pressure and discharge pressure on the mixing drum, providing CPU-accessible correlation values wherein peak discharge pressure is correlated with rheology of concrete discharged; and (i) providing an indication of a concrete property based on rheology of concrete discharged as determined by said CPU, (ii) treating the concrete in the mixing drum based on calculations by the CPU involving the determined rheology of concrete in the mixing drum based on measurement of peak discharge pressure, or (iii) performing both (i) and (ii).

In further exemplary methods, step (ii) further comprises treating the concrete in the mixing drum based on calculations by the CPU involving the determined rheology of concrete in the mixing drum based on measurement of peak discharge pressure, wherein the treated concrete is concrete remaining in the mixing drum after previous partial discharge, and the amount of remaining concrete is determined by employing an automated rheology monitoring system having a computer processor unit ("CPU"), the CPU being connected to at least one sensor for monitoring pressure for rotating the mixing drum, and the CPU being connected to a sensor for determining the number of mixing drum rotations, the CPU being programmed to calculate load size ("LS") based on the following formula: LS=OLS−(RR−RTD)*VPRUD wherein "OLS" represents the original load size of concrete in the mixing drum before said previous partial discharge of concrete from the drum; "RR" represents the number of drum rotations in the discharge direction required for said previous partial discharge; "RTD" represents the Revolutions-To-Discharge value which corresponds to the number of mixing drum rotations in the discharge direction required to commence discharge of concrete from the mixing drum, said number of mixing drum rotations being a function of concrete load size in the mixing drum; and "VPRUD" represents the Volume-Per-Revolution-Upon-Discharge value which corresponds to discharge rate of the concrete in terms of amount of concrete discharged for each mixing drum rotation in the discharge direction, the discharge rate of concrete being a function of the rheology of the concrete at the time of discharge; and OLS, RR, RTD, and VPRUD being stored in CPU-accessible location and employed by a CPU in calculating load size of the concrete remaining in the drum after previous partial load discharge.

In further exemplary methods, the automated concrete rheology monitoring system comprises CPU-accessible data values based on correlations between concrete rheology and fluid additions which are added into the concrete mix to alter said rheology, and further wherein peak discharge pressure is measured and used to calibrate the correlation between concrete rheology and fluid additions which are added into the concrete mix to alter said rheology.

An exemplary system of the invention for determining rheology of concrete, comprises: an automated concrete rheology monitoring system having a computer processing unit (CPU) connected electrically or wirelessly to a plurality of sensors for monitoring conditions on a concrete delivery vehicle having a mixing drum, including sensor for monitoring pressure on the mixing drum in the charge direction and sensor for monitoring pressure on the mixing drum in the discharge direction (and preferably having sensor for monitoring rotational speed of the mixing drum); CPU-accessible correlation values wherein peak discharge pressure is correlated with rheology of concrete discharged; and the CPU is instructed to calculate rheology of concrete contained in a mixing drum based on the CPU-accessible correlation values and to provide a report (of volume of concrete in the mixing drum or otherwise initiate an alarm if concrete condition or status departs from a target condition or status) of a concrete property based on rheology of concrete discharged as determined by operation of the CPU, and/or treating the concrete in the mixing drum based on calculations by the CPU involving the determined rheology of concrete in the mixing drum (e.g., such as by adding a dose of chemical admixture based on the determined rheology of concrete in the mixing drum).

The present inventors believe that monitoring of discharge pressure has not, until the present invention, been considered as useful for confirming concrete volume on the delivery truck. They have discovered that the discharge pressure can be used for confirming when concrete has been completely unloaded from the drum. Thus, an exemplary method of the present invention for determining when discharge of concrete from a delivery vehicle mixing drum is completed, comprises: monitoring discharge pressure for rotating the mixing drum in the direction of discharge, by employing a sensor which is in electrical or wireless combination with an automated concrete monitoring system having a computer processing unit (CPU); sensing when discharge pressure falls below a predetermined discharge pressure value stored into CPU-accessible memory or storage, said predetermined discharge pressure value corresponding with an empty mixing drum state; and reporting completion of the concrete discharge from the mixing drum.

For example, where the rotation rate of the drum in discharge direction is 2-5 revolutions per minute (RPM), the predetermined discharge pressure value is preferably between 100-400 RPM, and more preferably between 150-250 RPM.

In further exemplary embodiments, the number of mixing drum revolutions is monitored from start to finish of discharge of a concrete load, and the monitored number of drum revolutions is employed in revising or confirming accuracy of CPU-accessible data, including the Revolutions to Discharge value ("RTD") which corresponds to the number of mixing drum rotations in the discharge direction required to commence discharge of concrete from the mixing drum; and the Volume-Per-Revolution-Upon-Discharge value ("VPRUD") which corresponds to discharge rate of the concrete in terms of amount of concrete discharged for each mixing drum rotation in the discharge direction. Both the RTD and VPRUD values were previously explained above.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Skilled artisans can make variations and changes without departing from the spirit of the invention.

It is claimed:

1. A method for determining rheology of concrete, comprising:
in an automated concrete rheology monitoring system having a computer processing unit (CPU) connected electrically or wirelessly to a plurality of sensors configured for monitoring conditions on a concrete delivery vehicle having a mixing drum for concrete, including a sensor for monitoring discharge pressure on the mixing drum, performing the following steps:
monitoring discharge pressure of a concrete load discharged from the concrete mixing drum;
comparing the monitored peak discharge pressure of the discharged concrete load with CPU-accessible database wherein peak discharge pressure values correspond to concrete rheology values;
reporting a rheology value of the concrete discharged based on the peak discharge pressure as monitored; and
wherein said automated concrete rheology monitoring system further comprises CPU-accessible data comprising correlations involving concrete rheology values measured prior to discharge based on charge pressure and during discharge based on discharge pressure, and wherein said CPU determines whether to update the correlation involving charge pressure and concrete rheology values if the concrete rheology values measured prior to discharge based on charge pressure and measured during discharge based on discharge pressure differ by more than a pre-determined amount.

2. The process of claim 1 wherein said reporting comprises one or more of the following steps: (a) indicating said rheology value on a monitor screen and/or ticket; (b) providing an indication on a monitor screen and/or ticket confirming whether or not peak discharge pressure monitored corresponds to a rheology condition that coincides with target rheology specified for the concrete; or (c) performing (a) and (b).

3. The process of claim 1 further comprising treating concrete remaining in the concrete mixing drum after partial concrete load discharge, the load ("LS") being computed by the CPU based on the formula, LS =OLS−(RR−RTD) *VPRUD, wherein "OLS" represents the original load size of concrete in the mixing drum before said previous partial discharge of concrete from the drum; "RR" represents the number of drum rotations in the discharge direction required for said previous partial discharge; "RTD" represents the Revolution-To-Discharge value which corresponds to the number of mixing drum rotations in the discharge direction required to commence discharge of concrete from the mixing drum, said number of mixing drum rotations being a function of concrete load size in the mixing drum; and "VPRUD" represents the Volume-Per- Revolution-Upon-Discharge value which corresponds to discharge rate of the concrete in terms of amount of concrete discharged for each mixing drum rotation in the discharge direction, said discharge rate of concrete being a function of the rheology of the concrete at the time of discharge; and said OLS, RR, RTD, and VPRUD being stored in CPU-accessible location and employed by a CPU in calculating load size of the concrete remaining in the drum after a prior partial discharge.

4. The method of claim 1 further comprising:
using CPU-accessible data having correlation values between concrete rheology and fluid additions which are added into the concrete mix to alter said rheology, and wherein peak discharge pressure is measured and used to calibrate the correlation values between concrete rheology, as monitored by the system based on charge pressure when the drum is rotating in the mixing/loading direction and the fluid additions which are added into the concrete mix to alter the rheology of the concrete, the effect of such fluid additions being correlated with rheology as monitored by the system based on charge pressure when the drum is rotating in the mixing/loading direction.

5. The method of claim 1, wherein the rheology value is slump of concrete.

6. The method of claim 1, further comprising confirming that total amount of concrete discharged from the concrete mixing drum equaled the load size received in the mixing drum.

7. The method of claim 3 wherein calculation of the remaining load size is used to calculate or manage the amount of water or chemical admixture or admixtures to be added to the concrete in the mixing drum, the admixture or admixtures being selected from the group consisting of water-reducer admixture, set retarding admixture, accelerator admixture, and air entraining admixture.

8. The method of claim 3 wherein an alarm, monitor screen symbol, alert, or other indication is transmitted to a dispatch center, foreman at the construction site, supervisory architect, or driver of the truck or other trucks, corresponding to remaining concrete is available in the mixing drum and volume and slump of the available remaining concrete.

9. The method of claim 3 further comprising providing a paper or electronic ticket confirming quantity of concrete remaining in the mixer drum.

10. The method of claim 3 further comprising providing a paper or electronic invoice for disposal of concrete remaining in the mixer drum.

11. The method of claim 3 further comprising determining whether the concrete remaining in the mixer drum can be re-used based on factors selected from time since initial batching or loading at the concrete plant, the number of drum revolutions since initial batching or loading, temperature of concrete, quantity of water added to concrete, quantity and type of chemical admixture added to the concrete, the design strength of the concrete, and water-to-cement ratio.

12. The method of claim 1 wherein the rheological value is slump flow.

13. A method for determining rheology of concrete, comprising:
in an automated concrete rheology monitoring system having a computer processing unit (CPU) connected electrically or wirelessly to a plurality of sensors configured for monitoring conditions on a concrete delivery vehicle having a mixing drum for concrete, including a sensor for monitoring discharge pressure on the mixing drum, performing the following steps:
monitoring discharge pressure of a concrete load discharged from the concrete mixing drum;
comparing the monitored peak discharge pressure of the discharged concrete load with CPU-accessible database wherein peak discharge pressure values correspond to concrete rheology values;
reporting a rheology value of the concrete discharged based on the peak discharge pressure as monitored; and
treating concrete remaining in the concrete mixing drum after partial concrete load discharge, the load ("LS") being computed by the CPU based on the formula, $LS = OLS - (RR - RTD) * VPRUD$, wherein "OLS" represents the original load size of concrete in the mixing drum before said previous partial discharge of concrete from the drum; "RR" represents the number of drum rotations in the discharge direction required for said previous partial discharge; "RTD" represents the Revolution-To-Discharge value which corresponds to the number of mixing drum rotations in the discharge direction required to commence discharge of concrete from the mixing drum, said number of mixing drum rotations being a function of concrete load size in the mixing drum; and "VPRUD" represents the Volume-Per-Revolution-Upon-Discharge value which corresponds to discharge rate of the concrete in terms of amount of concrete discharged for each mixing drum rotation in the discharge direction, said discharge rate of concrete being a function of the rheology of the concrete at the time of discharge; and said OLS, RR, RTD, and VPRUD being stored in CPU-accessible location and employed by a CPU in calculating load size of the concrete remaining in the drum after a prior partial discharge.

14. The method of claim 13 wherein calculation of the remaining load size is used to calculate or manage the amount of water or chemical admixture or admixtures to be added to the concrete in the mixing drum, the admixture or admixtures being selected from the group consisting of water-reducer admixture, set retarding admixture, accelerator admixture, and air entraining admixture.

15. The method of claim 13 wherein an alarm, monitor screen symbol, alert, or other indication is transmitted to a dispatch center, foreman at the construction site, supervisory architect, or driver of the truck or other trucks, corresponding to remaining concrete is available in the mixing drum and volume and slump of the available remaining concrete.

16. The method of claim 13 wherein an alarm, monitor screen symbol, alert, or other indication is transmitted to a dispatch center, foreman at the construction site, supervisory architect, or driver of the truck or other trucks, corresponding to remaining concrete is available in the mixing drum and volume and slump of the available remaining concrete.

17. The method of claim 13 further comprising providing a paper or electronic ticket confirming quantity of concrete remaining in the mixer drum.

18. The method of claim 13 further comprising determining whether the concrete remaining in the mixer drum can be re-used based on factors selected from time since initial batching or loading at the concrete plant, the number of drum revolutions since initial batching or loading, temperature of concrete, quantity of water added to concrete, quantity and type of chemical admixture added to the concrete, the design strength of the concrete, and water-to-cement ratio.

19. A method for determining rheology of concrete, comprising:
in an automated concrete rheology monitoring system having a computer processing unit (CPU) connected electrically or wirelessly to a plurality of sensors configured for monitoring conditions on a concrete delivery vehicle having a mixing drum for concrete, including a sensor for monitoring discharge pressure on the mixing drum, performing the following steps:
monitoring discharge pressure of a concrete load discharged from the concrete mixing drum;
comparing the monitored peak discharge pressure of the discharged concrete load with CPU-accessible database wherein peak discharge pressure values correspond to concrete rheology values;
reporting a rheology value of the concrete discharged based on the peak discharge pressure as monitored;
wherein said automated concrete rheology monitoring system further comprising CPU-accessible data comprising correlations involving concrete rheology values measured prior to discharge based on charge pressure and measured during discharge based on discharge pressure; and
using CPU-accessible data having correlation values between concrete rheology and fluid additions which are added into the concrete mix to alter said rheology, and wherein peak discharge pressure is measured and used to calibrate the correlation values between concrete rheology, as monitored by the system based on charge pressure when the drum is rotating in the mixing/loading direction and the fluid additions which are added into the concrete mix to alter the rheology of the concrete, the effect of such fluid additions being correlated with rheology as monitored by the system based on charge pressure when the drum is rotating in the mixing/loading direction.

\* \* \* \* \*